US006114153A

United States Patent [19]

Shukla et al.

[11] Patent Number: 6,114,153

[45] **Date of Patent: *Sep. 5, 2000**

[54] HYDROPHOBIC PARTICLE-COATED AQUEOUS DROPLET REACTION CHAMBER

[76] Inventors: Ashok K. Shukla; Mukta M Shukla; Amita M Shukla, all of 10423 Popkins Ct., Woodstock, Md. 21163

[ * ] Notice: This patent is subject to a terminal disclaimer.

[21] Appl. No.: 09/360,581

[22] Filed: Jul. 26, 1999

[51] Int. Cl.[7] .............................. C12Q 1/68; C12P 19/34; C12N 13/00; G01N 27/26

[52] U.S. Cl. ............................ 435/91.2; 435/6; 435/91.2; 435/173; 204/403

[58] Field of Search .................................. 435/6, 41, 173, 435/91.2; 204/403

[56] References Cited

U.S. PATENT DOCUMENTS 5,773,238 6/1998 Shukla ...................................... 435/41

*Primary Examiner*—John S. Brusca
*Assistant Examiner*—Jeffrey S. Lundgren

[57] ABSTRACT

The present invention describes a reaction chamber consisting of a reactant-containing aqueous solution, which may be in droplet form, coated with a hydrophobic powder such as polytetrafluoroethylene, polypropylene, polyolefins, polyethylene or hydrocarbon-coated particles such as hydrocarbon-coated silica. The polymer particles are preferably less than 500 microns in size. Charcoal, metal powder or silica powder can be inserted inside or on the surface of the reaction chamber droplet. Also, a reaction chamber droplet containing a first reactant such as an enzyme-bound bead can be combined with a second reaction chamber droplet containing a second reactant to mix the reactants in the two chambers resulting in a subsequent reaction. A dialysis or filtration membrane can also be placed on a reaction chamber droplet for dialysis using the droplet chamber. Electrochemical reactions can be performed by placing the droplet chamber between two electrodes and producing current flow between them. A temperature-sensitive reaction such as Polymerase Chain Reaction (PCR) can also be performed by heating or cooling the droplet chamber. When the reaction chamber droplet is used for processes such as tissue culture, the use of this system reduces adhesion of the cells to the surfaces of a container.

20 Claims, 3 Drawing Sheets

HYDROPHOBIC PARTICLE-COATED AQUEOUS DROPLET REACTION CHAMBER

FIELD OF THE INVENTION

The present invention relates in general to chambers for chemical reactions, and in particular to the construction of such chambers through application of a hydrophobic powdered material to aqueous solutions.

The invention described and claimed herein comprises a novel chemical reaction chamber for carrying out reactions in aqueous solutions. Said chamber is characterized by an outer coating of one or more hydrophobic powdered materials such as polytetrafluoroethylene, polypropylene, polyolefins, polyethylene or hydrocarbon-coated particles such as hydrocarbon-coated silica.

BACKGROUND INFORMATION

In U.S. Pat. No. 5,773,238, the application of a fluoropolymer forming a droplet chamber has already been described.

Chemical and biochemical reactions are frequently carried out within a chamber or other container. In chemical and biochemical experiments, especially those involving small volumes (microvolumes) of a sample, there is always a significant loss of the sample as it disperses on the container walls.

Additionally, in reactions which are temperature sensitive, as for example the Polymerase Chain Reaction (PCR), there is also a loss of energy and time resulting from the need to heat (or cool) the reaction chamber itself.

However, when water or an aqueous solution contacts a hydrophobic powdered material, it forms droplets coated with the powder. These droplets form a reaction chamber that does not have significant sample loss or significant energy or time loss from the heating or cooling of a reaction chamber.

If a solid insoluble material such as active charcoal, metal powder, silica powder or a small piece of membrane or any other material is inserted inside or on the surface of the droplet reaction chamber, it will remain inside or on the surface.

By using a micro-pipette, liquid can be easily transferred from one droplet reaction chamber to another chamber. The sizes of the droplets can be increased or decreased by using a micropipette and eventually either by adding or removing the solution to/from the droplet reaction chamber.

These droplet reaction chambers can be used for different applications in chemical and biochemical reactions. In research laboratories, there are very often situations, when the container of the fluid can create problems while working with small volumes (in the microliter range). The droplet reaction chambers can be prepared in larger sizes by simply shaking the aqueous solution with the hydrophobic powder.

OBJECTS

The foregoing problems are overcome, and other advantages are provided, by a chemical reaction chamber comprised of an aqueous solution coated with a hydrophobic powder.

Among the objects of the present invention are to provide a new and useful chemical reaction chamber which does not rely on conventional walls to contain the chemical reaction and thereby to provide a new and useful chemical reaction method that reduces the loss of reactants and reduces the energy and time required to heat or cool the reaction.

These and other objects, which will be apparent from the discussion which follows, are achieved in accordance with the invention, by providing a novel chemical reaction chamber for carrying out reactions in aqueous solutions, characterized by an outer coating of a hydrophobic powdered material. The various features of novelty which characterize the present invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWING

The foregoing and still other objects of this invention will become apparent, along with various advantages and features of novelty residing in the present embodiments, from a study of the following drawings, in which.

DESCRIPTION OF THE PREFERRED EMBODIMENTS

Figure 1:
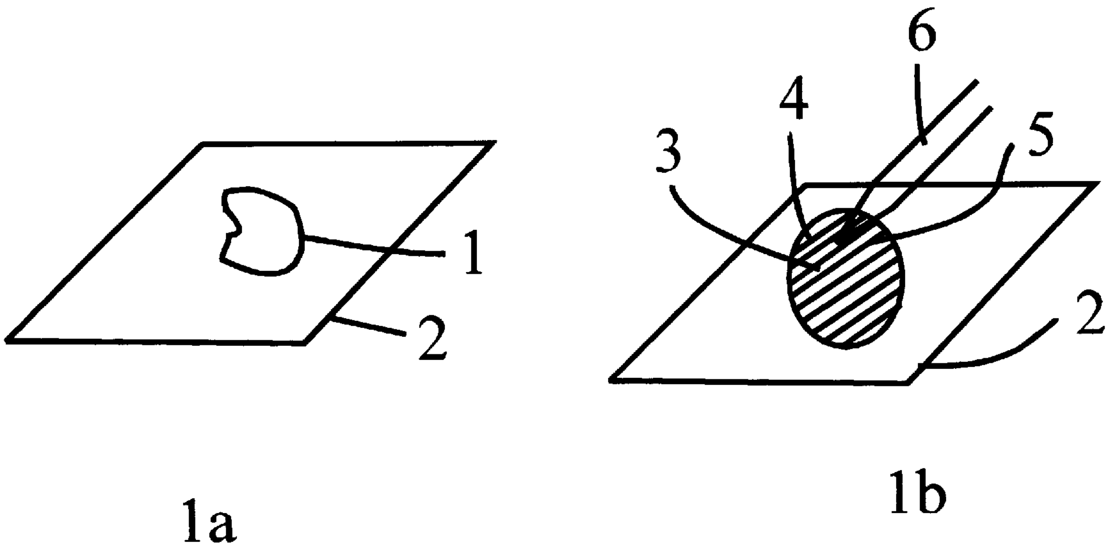
FIGS. 1*a* and 1*b* are a plane view of a droplet reaction chamber, contrasting an untreated droplet (FIG. 1*a*) with a treated droplet forming a reaction chamber (FIG. 1*b*).

Referring to the drawings, the invention is a novel chemical reaction chamber for carrying out reactions in aqueous solutions, characterized by an outer coating of a hydrophobic powdered material, shown in overview in FIG. 1. The operation of the invention is described with reference to a commonly available, inexpensive hydrophobic powdered material. It has been found that a preferred particle size is less than 500 microns. This is by way of illustration only, and the invention could be implemented using any suitable hydrophobic powdered material.

As shown in FIG. 1*a,* an aqueous solution (1) normally spreads out on the support surface (2). But, when an aqueous solution containing reactants of interest (3) is coated with a coating layer (4) of a hydrophobic powdered material, it forms a droplet reaction chamber (5).

The coating (4) causes the aqueous solution (3) to remain stable in a defined volume without the need for any external solid wall (except for a support {2}).

The reactants may be combined, then coated, or one reactant may be coated, and additional reactants introduced through the layer of hydrophobic powder (4). One method of doing so is by insertion using a pipette (6).

Similarly, a sample of the reaction product may be withdrawn through the layer of the hydrophobic powdered material (4), using for example a pipette.

Figure 3:
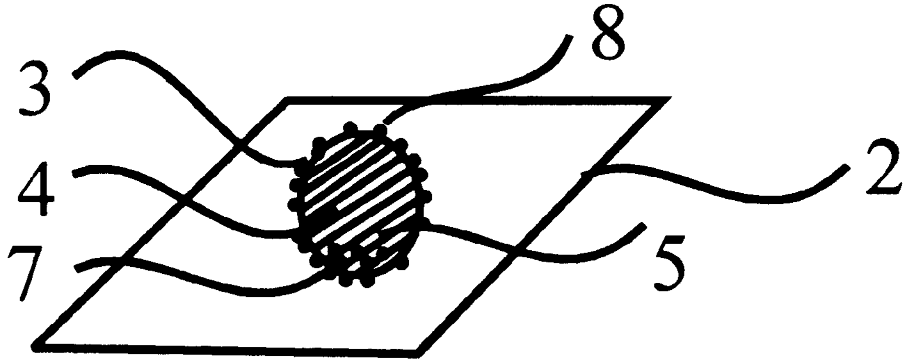
FIG. 3 illustrates a droplet reaction chamber with solid particles.

Referring to FIG. 3, in addition to reactants, the droplet reaction chamber (5) may contain solid particles, such as activated charcoal, a solid matrix for affinity purification, enzyme-bound beads for biochemical reactions, cells or tissue, either within (7) the droplet reaction chamber (5) or on its surface (8). Further processing of the droplet reaction chamber is possible. Examples include electroporation, electroelution and electrochemical reactions, which may be accomplished by simply placing the droplet reaction chamber between electrodes. Addition of metallic powder to the droplet reaction chamber increases the flow of electric current through the chamber.

The results of the chemical reaction may likewise be further processed, for example as follows. The droplet reaction chamber may be destroyed/taken apart either by the addition of a detergent, an organic solvent or any other substance that reduces surface tension. The coating of hydrophobic powdered material may then be removed from aqueous component by centrifugation, leaving the reaction product.

Alternatively, the droplet reaction chamber may be dried and subsequently reformed by the addition of water.

Specific applications of the invention are illustrated below.

Example 1

Use as a Chemical or Biochemical Reaction Chamber

By pipetting an aqueous solution, buffer or reaction mixture on PTFE powder, a droplet reaction chamber is formed. The droplet reaction chamber can be broken in different aliquots without the loss of materials. The reactions inside the droplet reaction chamber can be started or blocked by pipetting appropriate chemicals, such as biochemicals, enzymes or inhibitors, into the droplet reaction chamber. Once the reaction is completed, the droplet reaction chamber can be centrifuged in a container containing a filter having pores smaller than the particle size of the hydrophobic powdered material.

Example 2

Application in Equilibrium Dialysis

Figure 2:
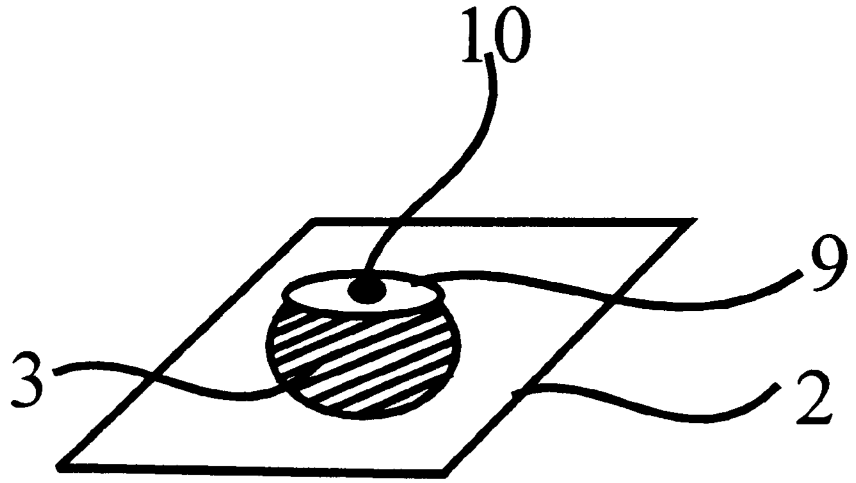
FIG. 2 illustrates a droplet reaction chamber with a membrane.

Referring to FIG. 2, if a membrane (9) is placed on a droplet reaction chamber (5), it floats along with the droplet reaction chamber (5). The lower surface of the membrane will be in contact with the liquid inside the droplet reaction chamber. A Liquid (10) may then be placed on the upper side of the membrane for dialysis. Once equilibrium has been reached, a sample may be taken from either side of the membrane by using a device such as a micropipette. Thus, the droplet reaction chamber may be used as a disposable dialyser for small samples.

Example 3

Combining Multiple Reaction Chambers

Figure 4:
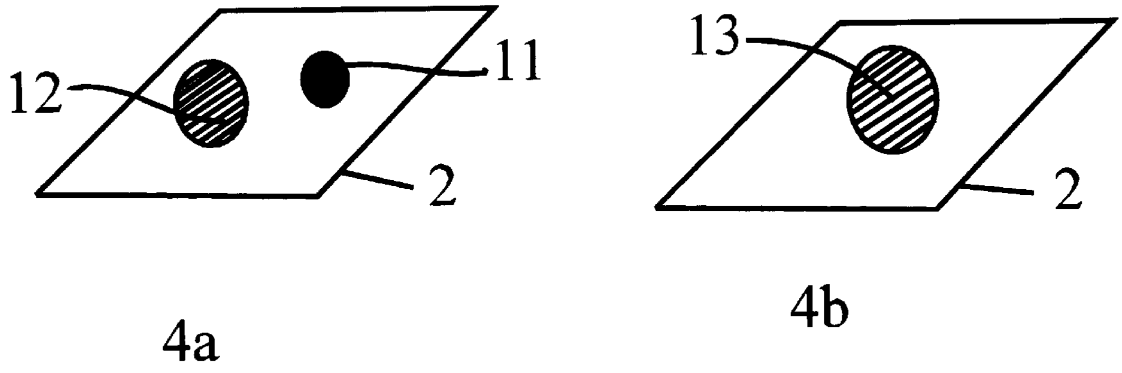
FIGS. 4*a* and 4*b* illustrate the fusion of two droplet reaction chambers (FIG. 4*a*) into a single droplet reaction chamber (FIG. 4*b*).

Referring to FIG. 4, two or more reactants may be combined as follows. Each reactant is coated with hydrophobic powdered materials as described above. The resulting droplet reaction chambers may then be combined by forcing them together, resulting in the rapid mixing of their contents. In FIG. 4*a,* two reactants are coated to form droplet reaction chambers (11) and (12), which are then combined to form a single droplet reaction chamber (13), in which a reaction between the contents of droplet reaction chambers (11) and (12) will occur, as shown in FIG. 4*b*.

Example 4

Rapid Temperature Change

In some reactions, notably PCR, it is necessary to rapidly vary the temperature of the reactants. Using a droplet reaction chamber, the heat and time otherwise expended on changing the temperature of a solid container are no longer expended thus increasing reaction time.

Example 5

Application in Tissue Culture Experiments

Many natural cells and cell lines have a tendency to stick to the surface of containers. By gently shaking a mixture of an aqueous solution containing such cells with a hydrophobic powdered material, the tendency to stick is reduced. Cells may be grown inside the hydrophobic powder coated aqueous phase suspension. In some cases, cell growth may be improved because of the three dimensional nature of the aqueous phase. A gentle shaking of the tissue culture container can evenly distribute the cells inside the chamber.

As can be seen from the above description and examples, it is possible to carry out a wide variety of chemical and biochemical reactions using this invention by coating appropriately sized droplets of an aqueous solution containing the desired reactants with a hydrophobic powder.

Thus, this invention describes a novel chemical reaction chamber for carrying out reactions in aqueous solutions, characterized by an outer coating of a hydrophobic powdered material, that has a number of novel features, and a manner of making and using the invention.

While a specific embodiment of the invention has been shown and described in detail to illustrate the application of the principles of the invention, it will be understood that the invention may be embodied otherwise without departing from such principles and various modifications, alternate constructions, and equivalents will occur to those skilled in the art given the benefit of this disclosure Thus, the invention is not limited to the specific embodiment described herein, but is defined by the appended claims.

What is claimed is:

1. A chamber for carrying out chemical reactions in aqueous solution, comprised of a droplet reaction chamber, said droplet reaction chamber comprising: an aqueous solution containing at least one reactant or reactant medium in droplet form; and, a coating of a hydrophobic powdered material on said droplet, which maintains said aqueous solution in droplet form.

2. A chamber as in claim 1, further comprising a support or housing for supporting or housing said droplet reaction chamber.

3. A chamber as in claim 1 wherein said hydrophobic powdered material is selected from the group consisting of polytetrafluoroethylene, polypropylene, polyolefins, polyethylene and hydrocarbon-coated particles.

4. A chamber as in claim 1 wherein said hydrophobic powdered material is silica bonded with hydrocarbons.

5. A chamber as in claim 1 wherein said hydrophobic material is a mixture of two or more hydrophobic powders.

6. A chamber as in claim 1 wherein said hydrophobic powdered material has a particle size of less than 500 microns.

7. A chamber comprising a droplet reaction chamber as in claim 1 and further comprising a filtration membrane in contact with said droplet reaction chamber said chamber is a dialysis chamber.

8. A method for carrying out chemical reactions, comprising the steps of: providing a first chamber as in claim 1 wherein said chamber contains a first reactant; providing one or more additional chambers as in claim 1 wherein said chambers contain additional reactants; and combining the chambers.

9. A method as in claim 8 wherein said first reactant comprises an enzyme-bound bead.

10. A kit for carrying out chemical reactions in the droplet reaction chamber of claim 1, comprising a hydrophobic powdered material, a container and reagents.

11. A method for culturing tissues in a droplet reaction chamber comprising the steps of: providing an aqueous solution containing biological cells in a container and coating said solution with a hydrophobic powder, thereby forming said droplet reaction chamber, whereby the droplet reaction chamber reduces adhesion between said tissues and said container.

12. A method for carrying out a temperature-sensitive chemical reaction, comprising the step of: providing a droplet reaction chamber as in claim 1 and heating or cooling said chamber to carry out said chemical reaction.

13. A method as in claim 12 wherein said temperature-sensitive chemical reaction is Polymerase Chain Reaction (PCR).

14. A method for chemical processing, comprising the steps of: providing a droplet reaction chamber containing a reactant as in claim 1; performing a reaction or chemical or biochemical process within said droplet reaction chamber; destroying/taking apart said chamber by adding a chamber-destroying substance; and removing the hydrophobic powder comprising said droplet reaction chamber by filtration and centrifugation.

15. A method as in claim 14 wherein said droplet reaction chamber is disrupted using a detergent.

16. A method as in claim 14 wherein said droplet reaction chamber is disrupted using an organic solvent.

17. A method for carrying out an electrochemical process comprising the step of: providing a droplet reaction chamber as in claim 1; placing said droplet chamber between two electrodes; and providing a current flow between the two electrodes to produce an electrochemical reaction.

18. A method as in claim 17 wherein said electrochemical process comprises electroporation.

19. A method as in claim 17 further comprising the step of placing metal particles within or on the surface of said droplet reaction chamber.

20. A chamber as in claim 3, wherein the hydrocarbon-coated particles are hydrocarbon-coated silica.

* * * * *